United States Patent [19]
Rakshit et al.

[11] Patent Number: 5,999,909
[45] Date of Patent: *Dec. 7, 1999

[54] METHODS FOR ESTABLISHING CERTIFIABLE INFORMED CONSENT FOR A PROCEDURE

[75] Inventors: Amitabha Rakshit, Longmont; Wilson A. Judd, Woodland Park, both of Colo.

[73] Assignee: Medical Training and Services International, Inc., Boulder, Colo.

[ * ] Notice: This patent is subject to a terminal disclaimer.

[21] Appl. No.: 09/124,859

[22] Filed: Jul. 31, 1998

Related U.S. Application Data

[63] Continuation of application No. 07/886,384, May 19, 1992, Pat. No. 5,799,282.

[51] Int. Cl.$^6$ ............................... G06F 17/60; G09B 3/00
[52] U.S. Cl. ................................................. 705/2; 434/350
[58] Field of Search ....................... 705/1, 2, 3; 434/219, 434/224, 307, 309, 321, 323, 350

[56] References Cited

U.S. PATENT DOCUMENTS

| | | | |
|---|---|---|---|
| 3,946,503 | 3/1976 | Buchan et al. | 434/316 |
| 4,359,223 | 11/1982 | Baer et al. | 463/2 |
| 4,360,345 | 11/1982 | Hon | 343/262 |
| 4,395,236 | 7/1983 | Gotthold | 434/219 |
| 4,459,114 | 7/1984 | Barwick | 434/307 R |
| 4,475,132 | 10/1984 | Rodesch | 386/92 |
| 4,518,267 | 5/1985 | Hepp | 368/107 |
| 4,569,421 | 2/1986 | Sandstedt | 186/39 |
| 4,593,904 | 6/1986 | Graves | 463/9 |
| 4,602,907 | 7/1986 | Foster | 434/337 |
| 4,671,772 | 6/1987 | Slade et al. | 434/219 |
| 4,685,122 | 8/1987 | Deveson et al. | 379/90.01 |
| 4,771,344 | 9/1988 | Fallacaro et al. | 386/97 |
| 4,812,125 | 3/1989 | Strashun | 434/224 |
| 4,828,500 | 5/1989 | Seidel et al. | 434/247 |
| 4,828,501 | 5/1989 | Ingenito et al. | 434/265 |

(List continued on next page.)

FOREIGN PATENT DOCUMENTS 0320749  6/1989  European Pat. Off. .

OTHER PUBLICATIONS

Patient Consent Form; Approved by the Colorado Medical Society Risk Management Committee.

Informed Consent? Plastic Surgeons Had Warnings on Safety of Silicone Implants; J. Rigdon; Wall Street Journal; Mar. 12, 1982; A1,A8.

Doctors Turn to Software to Avoid Malpractice Suits; G. Ruffenach; Wall Street Journal; approx. Mar. 2, 1992.

Videos, Questionnaires Aim to Expand Role to Patients in Treatment Decisions; R. Winslow; Wall Street Journal; Mar. 1992;B1,B3.

(List continued on next page.)

*Primary Examiner*—Stephen R. Tkacs
*Attorney, Agent, or Firm*—Luke Santangelo; Santangelo Law Offices, P.C.

[57] ABSTRACT

A method for establishing certifiable patient informed consent for a medical procedure, where, in one embodiment, the patient interacts with a video training system until mastery of all required information is successfully achieved. Training techniques which permit elicitation of measurable behaviors from a patient as a guide to discerning the level of knowledge of the patient are utilized. Certification is only granted when the measurable behavior approximately coincide with the legal and medical standards for establishing informed consent. The system is capable of adapting to various medical procedures, as well as various patient attitudes and knowledge bases, while still maintaining a level of consistency throughout. In one embodiment, a minimum probability of understanding may be preset, and the training procedure will continue until the actual statistical probability of understanding is at least equal to the preset minimum. An interactive nature of the system is present in the present system for facilitating the training process and continuously monitoring the patient's knowledge.

20 Claims, 5 Drawing Sheets

U.S. PATENT DOCUMENTS

| | | | |
|---|---|---|---|
| 4,839,743 | 6/1989 | Best et al. ................................. | 386/31 |
| 4,846,693 | 7/1989 | Baer ........................................ | 434/308 |
| 4,863,384 | 9/1989 | Slade ....................................... | 434/107 |
| 4,895,376 | 1/1990 | Shiung-Fei ............................... | 463/2 |
| 4,907,146 | 3/1990 | Caporali .............................. | 395/200.34 |
| 4,907,973 | 3/1990 | Hon ......................................... | 434/262 |
| 4,930,019 | 5/1990 | Chu .......................................... | 386/96 |
| 4,931,018 | 6/1990 | Herbst et al. ............................ | 434/234 |
| 4,948,371 | 8/1990 | Hall ......................................... | 434/21 |
| 4,959,734 | 9/1990 | Foster ...................................... | 386/106 |
| 5,002,491 | 3/1991 | Abrahamson et al. .................. | 434/322 |
| 5,006,987 | 4/1991 | Harless .................................... | 434/323 |
| 5,025,374 | 6/1991 | Roizen et al. ........................... | 600/300 |
| 5,033,969 | 7/1991 | Kamimura ............................... | 434/322 |
| 5,035,625 | 7/1991 | Munson et al. .......................... | 434/332 |
| 5,059,127 | 10/1991 | Lewis et al. ............................. | 434/353 |
| 5,167,506 | 12/1992 | Kilis et al. ............................... | 434/262 |
| 5,267,865 | 12/1993 | Lee et al. ................................. | 434/350 |

OTHER PUBLICATIONS

FFR Offers Computer–Generated Patient Education Aid Program; Family Practice Recertification; B. MacKenion; Feb. 1992; p. 17.

Tips from Other Journals; American Family Physician; Feb. 1992; p. 829.

Infor. Seeking & Interactive Videodisc Preparation for Third Molar Extraction; Jour. of Oral Maxillofacial Surg; D. Ader; 1991; 27–32.

CBT Options–Solutions & Systems; Civil Aviation Training; T. Nash; pp. 38–43.

Big is Beautiful–Pilot Training at American Airlines; Civil Aviation Training; D. Saw; 1991; pp. 4–6.

Military Training Programs; Military Standard; U.S. Goverment—Department of Defense; Dec. 1990; pp. 1, 65–73.

Participatory Risk Management Program; COPIC; Jun. 1990;pp. 1–6.

Surgical Informed Consent: What it is and is Not; Amer. Journal of Surgery; W. Sterling Edwards; Apr. 1987; pp. 574–578.

Advanced Aircrew Training System (AATS); Func. Design Descrip.; Seville Technical Document TD 87–12; K. R. Williams, et al.; Oct. 1987; pp. 3–1,2,3,4,5,3–13,3–24,3–25.

Training—Instructional System Development; Air Force Manual 50–2 U.S. Goverment–Dept. of Air Force; Jul. 1986; pp. 23–31.

Chapter 30 Consents; Operating Room Admin. Manual; various contributors; approx. 1990; 30:1–30:26.

An Approach to the Evaluation of Tailored Testing; Research Report; Kathleen Daubek, et al.; Dec. 1973; pp. 1–12.

Hume; "A Dynamic Student Model in a Cardiovascular Intell. Tutoring System"; Jun. 14, 1992; pp. 370–377.

Harris; "IEEE Engineering in Medicine and Biology Society;" Nov. 4, 1988.

Strickland et al.; "Developing a CAI Graphics Simulation Model: Guidelines"; T H E Journal; v16 n7; p. 88(5); Mar. 1989; Dialog: File 275, ACC#01293856.

Davis et al.; "The Gap Between Patient Reading Comprehension and the Readability of Patient Education Materials"; Journal of Family Practice; v31 n5; p. 533(6); Nov. 1990; Dialog: File 149, ACC#9213052.

Dialog Abstract: Kearsley et al.; "Microcomputer–based Training in Business and Industry: Present Status and Future Prospects"; Journal of Educational Technolgy Systems; v10 n2: pp. 101–108; 1981–1982; Dialog: File 2, Acc#01860303.

Dialog Abstract: Gayeski; "Interactive Video: Integrating Design Levels and Hardware Levels"; Journal of Educational Technology Systems; v13 n3; pp. 145–151; 184–185; Dialog: File 2, Acc#02475642.

Goldes; "Acronyms for Education"; PC Magazine; v3 n7; pp. 353–355; Apr. 17, 1984 Dialog: File 148, Acc#02057293.

Smith; "How to Design Interactvie Training Programs"; Training; v20 n12; pp. 30–45; Dec. 1983.

"Videotape Aids Informed Consent Decision" by Barbour et al. Dec. 15, 1978 pp. 2741–2742.

METHODS FOR ESTABLISHING CERTIFIABLE INFORMED CONSENT FOR A PROCEDURE

This is a continuation of Ser. No. 07/886,384, filed May 19, 1992, nowe U.S. Pat. No. 5,799,282.

I. FIELD OF THE INVENTION

The present invention relates to methods for establishing informed consent to a medical procedure, particularly for medical procedures such as a hysterectomy, a blood transfusion, AIDS/HIV treatment, psychiatric treatment, dental procedures, anesthesia, and the like. More specifically, the present invention relates to interactive methods for establishing within a predetermined probability that a patient, or his/her guardian, has understood the disclosed information regarding the medical procedure.

II. BACKGROUND OF THE INVENTION

Virtually every medical procedure performed in the United States, including psychiatric treatment and dental procedures, requires that the patient consent to the procedure. This consent may either be expressed or implied. A competent adult patient can implicitly consent to a procedure by his/her situation or his/her actions. Examples of this type of consent would include certain emergencies and typical physical examinations. Consent to such procedures is implied by the patient. While it is frequently deemed acceptable, it is not the type of consent preferred by the medical community and is to be avoided where possible.

Expressed consent is preferred by the medical community. At present, expressed consent is usually oral or written. The inherent difficulty in proving details with respect to oral consent makes this type of expressed consent less preferable for most health care providers. Using existing techniques, many non-emergency type surgical procedures require the patient to read and sign an "informed consent" form. Admittedly, this can be awkward; it is well established, however. For example, the "Operating Room Administration Manual—Checklists, Guidelines & Forms" includes a checklist of clauses which may be included in the typical written consent form. In addition, a list of medical procedures requiring full disclosure is included as Exhibit 30-3 to this reference. These procedures, among many others, are deemed to require not merely consent, but informed consent.

The author of an article discussing surgical informed consent suggests to establish legally-sufficient informed consent, at least three elements are required: (1) sufficient information in understandable terms, (2) competence on the part of the patient to reason, and (3) absence of coercion. (This reference, disclosed below, contains much authoritative material on the subject of informed consent.)

These legal requirements can be burdensome to the medical practitioner. Not only does complying with such requirements take time, but the constantly changing state of the law makes merely remaining current in this developing field a challenge. When properly fulfilled, it is even possible that the health care provider could spend more time obtaining consent to avoid lawsuits than practicing medicine. The present invention is designed to alleviate this imposition on medical personnel by providing a method of establishing certifiable informed consent. The disclosed system and methods improve the ability of achieving an "informed" state, the credibility of having received "consent", and enhance the ability to prove in a court of law that informed consent was indeed established, should it be necessary.

For many years the only device used to indicate possible informed consent was a standard form, as mentioned previously. In some instances the form served as a reference guide for the practitioner as he/she read from it to the patient. In other instances the form might have been handed to the patient along with a multitude of other forms, each requiring the patient's signature. It is very likely that, in haste, many of these informed consent forms are signed without ever having been read; even more likely is the fact that such forms are rarely truly understood by the patient. One study has shown that on the average patients read 4.6 grade levels below their reported highest grade completed. The mean reading level in some communities was reported as low as third grade, with consent forms requiring a postcollege reading level (*Southern Medical Journal*, October 1991, vol. 84, p. 1172). This combined with the possible recklessness on the part of the patient, as well as the medical provider, fueled by the litigious nature of our society, has contributed to the skyrocketing malpractice insurance fees experienced by many health care providers. These are, naturally, passed on to the patient in the way of higher medical fees charges. Most acutely however, the signed informed consent form technique has failed in its primary purpose. Often it has not been deemed to sufficiently establish true "informed consent" by the patient.

To overcome this potential impact, written forms are often accompanied by a verbal explanation or interview by the health care provider. This solution is undesirable for at least two reasons. First, it reintroduces the oral element in obtaining a consent. Second, unfortunately, informed consent interview techniques are not an area focused upon by most medical schools. Instead, new practitioners are usually expected to observe, assimilate, and personalize what other colleagues do. While to a patient this interview may be no less important than the procedure itself, the health care provider may view it as a bothersome task that has little relevance to the procedure to be performed.

Even the standard informed consent forms currently used have often fatal practical limitations. They can be inconsistently applied. Typically the forms are modified for each specific medical, dental or psychiatric procedure. While this is efficient, it rarely takes into account the impacts of the differing information to be conveyed, the differing manners in which it must be delivered (if read), and the differing attitudes of the patient. Each of these naturally affect the dependability of the form. In addition, as each doctor tries to alter a general form for a specific procedure, personal biases can detract from the real goal of the process. Even if each of these limitations were recognized, until the present invention, it simply would not have been practical to tailor a document not only doctor to doctor, but also from day to day, and from patient mood to patient mood. This latter aspect—that a given patient might have different needs from day to day or hour to hour—has been an aspect that, until the present invention, those skilled in the art could not readily address. Those skilled in the art, the doctors and lawyers, simply believed it was not possible to accommodate the needs of the patient to this degree. While the need for controlled consistency in this area has been openly sought by consumer protection groups, medical groups, and malpractice insurance carriers, until the present invention it was not deemed practical to attempt to utilize a technique which could be varied to suit each specific occasion.

In order to meet these needs, the present invention utilizes techniques not traditionally applied to the informed consent field. Among these techniques is the use of video technology. The use of video as a training tool has been known and widely accepted in a number of fields. U.S. Pat. Nos. 4,360,345 and 4,907,973, both to Hon, disclose the use of computer/video systems for teaching health and medical education. U.S. Pat. No. 4,459,114 to Barwick discloses the use of video to teach communication skills, while U.S. Pat. No. 4,948,371 to Hall has applications in law enforcement training and military training. As the present invention recognizes, the video system's ability to provide consistency through controlled presentation can be beneficially applied to the informed consent field as well. Video tape (VHS or beta) and video disk systems have been used in some hospitals, clinics and doctor offices, functioning to educate patients on a limited number of medical procedures. None, however are used to address the very important aspect of certifying or proving the patient had, without question, given his or her informed consent. Given this known use of such a system, it might initially be considered surprising that the application of such a technology to the informed consent field was not recognized. This, however, may be a result of the diverse perspectives of the techniques traditionally involved.

The technology of using video as a training aid has been distinct from that of establishing informed consent. This is due to the goals involved, and may be highlighted by the goals of "teaching" and "training." The Oxford English Dictionary defines training as "bringing a person to a desired state or standard of efficiency by instruction and practice." Teaching on the other hand, is merely a process of conveying information. While most patients would sit through a short film on the risks and alternatives as related to a hysterectomy, few would view such a video with the intent of being trained. Merely presenting a video would not significantly overcome the limitations of the prior art. For example, while the entire procedure may be explained in detail, the patient is capable of "tuning out" certain information—just as he/she might-ignore or overlook the statements of a doctor. In this case the medical practitioner may believe he/she has satisfied his/her responsibilities when in fact the patient is not truly consenting in an informed manner. The present invention overcomes this limitation by devising a method for certifying not only the level of information conveyed to a patient, but the patient's level of understanding as well. The patient simply cannot be certified by the present invention and still have failed to understand the necessary aspects of the procedure.

Another problem with both the informed consent form, and standard education video is the extent of the information. Too little, or too much information can be detrimental to the process of establishing informed consent. While most systems and forms might hope to err on the side of too much information, this "overkill" may cause a patient to fail to fully comprehend important elements. Naturally, too little information would also fall short on the informed side of the issue. According to a December 1987 article from *The American Journal of Surgery*, entitled "Surgical Informed Consent: What It Is and Is Not", by W. Sterling Edwards, M.D., et al., the courts have utilized two concepts as guidelines for the degree of information that must be provided to a patient—the professional standard and the lay standard.

The professional standard has been suggested to require that the medical practitioner disclose what is standard for the community. As the more objective rule, it is used by the majority of jurisdictions. The lay standard, known also as the material risk standard, has been suggested to require the practitioner to disclose what any reasonable person would want to know about the procedure. With respect to what type of information must be disclosed, the two standards are in agreement that the information need not be encyclopedic, and that any possible serious conditions, no matter how remote, should be disclosed. With both the standard informed consent form and the continuous video type patient education system, a patient is virtually locked into the presentation process. If it is too much information, the patient must usually endure. If the information conveyed is deficient, it falls to the patient to glean additional information from another source, such as a doctor or nurse. The present invention avoids placing this burden on the patient. Instead, through interaction with the patient, the information provided can be personalized to the patient's knowledge base regardless of which standard is utilized.

Documentation of consent is usually not required by law. Obviously, though, if a suit is filed against a practitioner, the more documentation available, the better. In many instances, both the patient's and the doctor's recall of the information presented can be poor and unreliable. Thus, a signed document may be the only evidence to reliably evidence consent. The question still remains as to whether such consent was "informed", however. Did the practitioner read over all elements of the form? Did the patient? If either party read the form, did the patient understand the various terms used? Naturally, in a mere video presentation, similar concerns would arise. Prior to the present invention, reproducing the events that transpired up to the point of signature was very difficult if not impossible. The present invention overcomes this limitation to protecting both parties before consent can be established.

The present invention, in its various methods, recognizes and addresses these and other problems and overcomes many limitations encountered by those skilled in the art by bringing together, and bridging the gaps that have existed between the legal, medical, consumer and training fields with respect to establishing certifiable informed consent. Many devices and procedures have taught education of patients in the area of medical procedures. However, these devices and procedures have typically considered only the consumer (patient) groups and the medical field. Other approaches have taken the perspective of the legal field in attempts to protect medical practitioners and their insurance carriers. Until the present invention, no one had taken the approach of training and certifying patients' knowledge in a pending medical procedure, despite the long felt need for such certification, and the existence of the necessary implementing arts. Certainly problems such as proving "informed consent" exist in the field of informed consent (it might not be such a heavily litigated field otherwise), but such problems have gone unnoticed by those skilled in the art. Basically attempts at establishing patient informed consent were inadequate because those skilled in the art failed to address and balance the needs of the patient, the doctor, the court system, and the insurer. The recognition by the present inventors that the problems encountered in the informed consent field could be solved by applying and modifying techniques of a training nature, and not an educational nature, lead to the present invention. While other aspects of these training techniques have been known for some time, and while they have been used in various other fields, those skilled in the art of establishing informed consent have failed to recognize their value as solutions in the informed consent field. The prior art has taught away from the present invention by stressing education of patients rather than training. Other areas of teaching away by the prior art are rooted in the desire for a single general form, rather than a process which adapts to the continuously varying characteristics of procedures, doctors, patients, and courts. Rather than supplying a system which affords only an incremental increase in performance and design over the prior art, the present invention utilizes techniques which were not previously considered to achieve leaps in performance compared to the prior art.

III. SUMMARY OF THE INVENTION

The present invention discloses methods for establishing patient informed consent in conjunction with most medical procedures, such as used in hospitals, clinics, and doctors' offices. The disclosed methods provide a reliable and effective means for certifying each patient's level of understanding with respect to information furnished on a pending medical procedure. This invention serves to establish a patient's consent to a medical procedure by applying training techniques, to facilitate learning, and to monitor the state of knowledge by providing an interactive system.

In general terms, the invention involves various embodiments of a training technique for certifying informed consent. Many of the steps of this procedure achieve several different objects which, when combined, act to achieve the mentioned leaps in performance. In one instance, the invention takes into account legal and medical requirements for establishing informed consent while providing an interactive training process to allow optimal comprehension by the patient. The invention may also involve periodic testing which permits the patient's knowledge to be confirmed and correlated against predetermined minimums for understanding. Still other features of the present invention include closed-loop testing, which allows for the realization of the predetermined minimums, and various training media.

Accordingly, the present invention provides a method which establishes certifiable patient informed consent. It acts to provide both medical practitioners and patients with a competent training system. The system may include an interactive video disk which may interact with the patient through question and response techniques which help to elicit measurable behaviors from the patient. In addition, accepted medical and legal standards can be used to establish parameters in the system.

It is therefore broadly an object of the present invention to establish certifiable patient informed consent for a medical, dental or psychiatric procedure. A system may be designed which utilizes scientific training methods as a basis for interacting with the patient. By using these training methods, the patient's level of knowledge in the various areas of the procedure may be monitored. Consequently, each patient can be certified as having understood, within a predetermined probability, and consented appropriately to the medical procedure. In addition, medical and legal standards for establishing informed consent are typical reference parameters considered as the system is designed.

It is another object of the present invention to design a system which is capable of training a patient on various aspects of a medical procedure in an attempt to certify a patient's informed consent. A closed-loop system is used so that any patient not achieving the desired level of understanding continues to be trained until such a level is achieved. It is therefore an object of the present invention to periodically test the patient's knowledge of the conveyed information. The purpose of this periodic testing is to force the patient to prove their understanding of the information.

It is still another object of the present invention to elicit from the patient various measurable behaviors which may be correlated to the medical and legal standards utilized for establishing informed consent. This may be achieved by the periodic testing, mentioned previously, which may incorporate any type of question and response format, such as, but not limited to, multiple choice, true/false or essay. Likewise, the interactive nature of the system may be accomplished by numerous types of training media.

It is yet another object of the present invention to provide a system which is capable of certifying or proving the patient's level of knowledge. The present invention achieves this by capturing the patient's responses, and storing these responses. By doing so, any questions as to what the patient understood can be easily recalled and related as a probability. In this fashion the invention meets a goal of correlating probabilities to establish a more defensible informed consent.

Naturally, further objects of the invention are disclosed throughout other areas of the specification and claims.

IV. BRIEF DESCRIPTION OF THE DRAWINGS

The following descriptions and referenced drawings are for selected preferred embodiments of the present invention. Naturally, changes may be made to the disclosed embodiments while still falling within the scope and spirit of the present invention and the patent granted to its inventors.

V. DETAILED DESCRIPTION OF THE PREFERRED EMBODIMENTS

Figure 1:
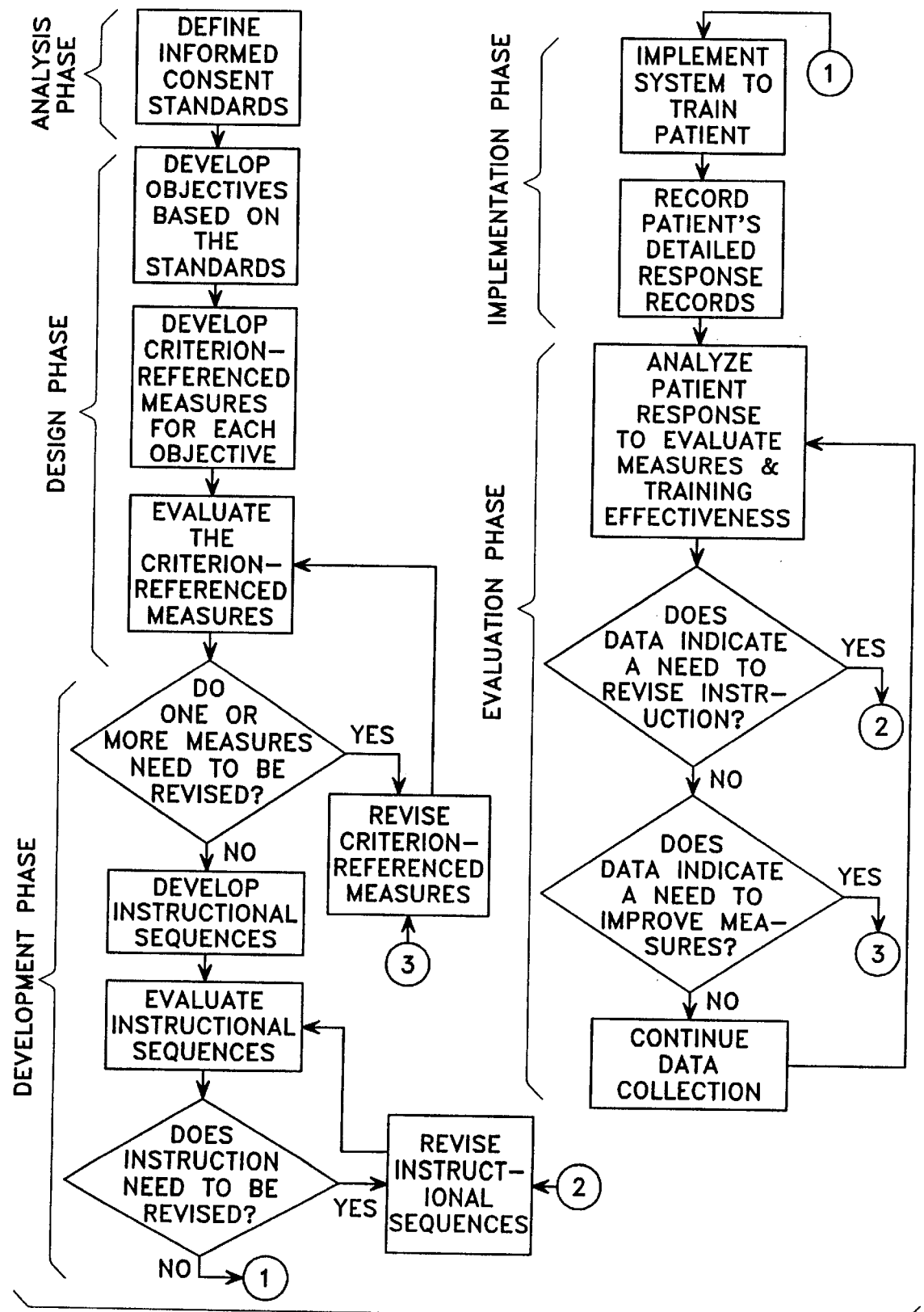
FIG. 1 is a flow chart diagram showing one possible embodiment of the instructional system development (ISD) process.

As can be seen from the drawings, the basic concepts of the present invention may be embodied in many different ways. FIGS. 1 through 5 show flow diagrams which illustrate different approaches of the present invention, in both design and interaction process, to certify informed patient consent to a medical procedure. The process is designed to result in a condition that is sufficient to "certify" that the patient was adequately informed when signing a consent form. To "certify" it is intended that a point should be reached by the patient such that he/she has achieved at least a predetermined minimum criterion that the information was understood. Naturally, the minimum would be set at a level consistent with the goals of the present invention. Medical procedures are understood to include dental procedures and psychiatric treatments among others which may require disclosure to the patient before beginning. While particular embodiments of the invention will be described, it will be obvious that changes and modifications may be made without departing from the broad aspects of the present invention.

Before beginning the process of certification, requirements and standards must first be established. The system of the present invention uses a variation of a known training design and development technique called instructional system development (ISD). ISD is a systematic approach to the design, development, and continued refinement of instruction. The ISD model is explained in detail in a number of published references, including *Instructional System Development*, printed on Jul. 15, 1986, by the United States Department of The Air Force; *Systems Engineering Applied To Training* by Silvern, published in 1972; *The Systematic Design Of Instruction* by Dick, et al, published in 1978; and, *Instructional Product Development* by Baker, et al, published in 1971. These articles are hereby incorporated by reference into the discussion of this application.

One embodiment of the ISD process used in the present invention may be summarized as follows:

(1) Establish, through analysis, the body of information that a patient might need to know about a particular medical procedure in order for them to legally and ethically be considered to be "informed";

(2) Establish a set of observable, measurable "objectives" which, if these objectives are achieved or "mastered", indicate that the patient comprehends this information and can apply it to his/her own situation;

(3) Develop, for each objective defined in step 2, a set of interactive behavioral measures (e.g., questions and patient answers to these questions) that evaluate whether or not the patient has met the objective;

(4) Evaluate the measures developed in step 3 with respect to their ability to discriminate persons who are knowledgeable about the procedure from those who are not;

(5) Develop a sequence of interactive, individualized instructions designed to facilitate patients' mastering the objectives established in step 2 (i.e., train them to provide the correct responses to the measures developed in step 3);

(6) Evaluate the effectiveness of the instruction and revise the instruction to correct any deficiencies;

(7) Implement the interactive sequences developed in steps 2 through 6 with actual patients. During the interaction with each patient, estimate the probability that the patient has mastered each objective. If the probability that the patient has mastered an objective does not meet or exceed a predetermined criterion, present additional instruction pertaining to that objective and repeat the evaluation;

(8) Collect detailed data on actual patients' responses in interacting with both the instruction and the measures. Use this data to refine both the measures and the instruction.

Figure 2:
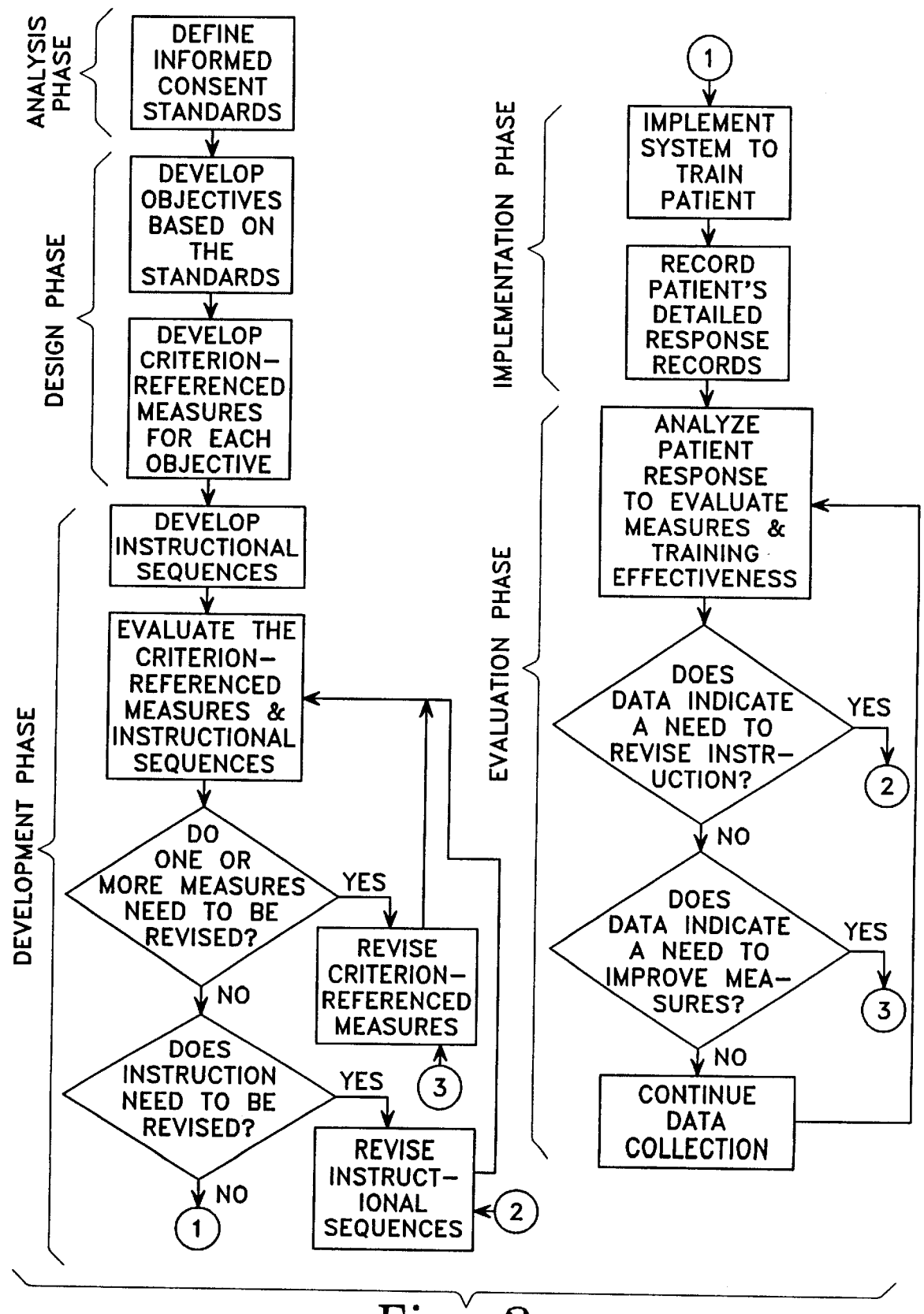
FIG. 2 is a flow chart diagram of another possible embodiment of the ISD process.

ISD, as shown in FIGS. 1 and 2, begins with the "analysis phase." The development of the present embodiment may be commenced through careful evaluation of both legal and medical requirements for establishing informed consent. Such legal requirements may include, among others, those that are statutorily dictated by state or federal governmental bodies, those that have been developed by case law in various jurisdictions, and those that have been sanctioned by the American Medical Association (AMA) or some other medical field governing body. The analysis includes evaluating all types of information relevant to a medical procedure and then selecting those items of information which are considered necessary for establishing informed consent. Since these requirements may be broadly phrased and ambiguous in meaning, more definite parameters may be derived from these requirements. The present invention translates requirements into specific statements or standards deemed to be representative of the requirements. These may be statements concerning patients' knowledge about specific medical procedures, knowledge of the benefits and risks of these procedures, and the patients' ability to apply this knowledge to their own situation. For instance, a court decision may result in new or altered requirements. These new or altered requirements would be translated into one or more specific standards. As these standards are translated—based on precedent and accepted medical protocol—measurable patient behaviors, or objectives, may be defined.

This begins the next step of ISD, called the "design phase." In this phase, objectives are developed based upon the applicable standards. Each objective specifies the observable behavior(s) that would be expected from an informed patient in response to a specific situation. For example, an objective might state that an informed patient would, when presented with a list of surgical risks, correctly recognize those risks associated with the surgical procedure under consideration. These objectives, in the present embodiment, are designed to correlate with or approximate as closely as possible the standards defined during the analysis phase. The validity of this translation or correlation can be evaluated frequently, and the objectives may be altered or refined to better approximate the estimated standard.

A second aspect in the "design phase" is to develop, for each objective, a set of interactive behavioral measures (e.g., questions and patient answers to these questions) that evaluate whether or not the patient has met the objective. These interactions are designed as criterion-referenced measures. Criterion-referenced measures are designed to yield measurements that are directly interpretable in terms of specified performance standards (i.e. Is the respondent capable of performing the task represented by the corresponding objective? Does the respondent possess the knowledge required by the corresponding objective?). They are to be contrasted with the more commonly used norm-referenced measures (i.e., typical aptitude and achievement tests). The latter are designed to compare respondents with each other to rank them with respect to a particular set of skills or knowledge. *Criterion-Referenced Measurement* by James W. Popham, published in 1971, provides detailed discussion on this type of measurement. To supplement the background of this application the Popham reference is hereby incorporated by reference.

In the instances and applications of the present invention where the defined behaviors are elicited responses to stimuli, such as questions or statements, a statistical probability can be calculated to determine whether the objective has been achieved. The calculation may be as simple as a percentage of correct answers, or may, of course, be a more complex statistical calculation which may take into account aspects such as standard variance, normalization, random chance, error analysis, etc. In other instances the predetermined minimum criteria may be achieved to the satisfaction of a training expert, or the like. In addition to the ISD model training techniques, the present invention may also make use of artificial intelligence techniques for training and evaluation. Each of these techniques is known and implementable by any person with reasonable skill in the field of training.

A third aspect in the "design phase" can be to evaluate the criterion-referenced items to measure their ability to discriminate persons who have met the objective from those who have not met the objective. This may be accomplished through tryouts with two groups of persons: one group that can be assumed to be fully informed regarding the medical procedure (e.g., medical interns, practicing physicians) and one group that can be assumed to be uninformed about the procedure (e.g. high school students). The tryout results for each item could be evaluated as shown in Table I and described below.

In this hypothetical example, the item being validated has been administered to 30 members of each group. Ideally, all members of the Group A (the "Informed Group") would answer the item correctly and all members of the Group B (the "Uninformed Group") would answer it incorrectly. In practice, however, an uninformed person may answer correctly because of an inadvertent clue in the item or a lucky guess. An informed person may answer incorrectly due to a poorly phrased question or through carelessness.

TABLE 1

| Responses | Informed Group | Uninformed Group | Totals |
|---|---|---|---|
| Correct | 27<br>$p = 27/30$<br>$= .90$ | 5<br>$p = 5/30$<br>$= .17$ | 32 |
| Incorrect | 3<br>$p = 3/30$<br>$= .10$ | 25<br>$p = 25/30$<br>$= .83$ | 28 |
| Totals | 30 | 30 | |

(Example of Validation Data For A Measurement item)

If there is a sufficient difference between the response patterns of the Informed and Uninformed Groups (as there is in this case), the item is considered to discriminate between groups and is retained. Otherwise, the item is dropped or revised and re-evaluated.

Naturally establishing even a 100% probability of patient understanding of the information provided is not helpful if the information provided is not all that is required for the particular medical procedure. The next step therefore, which begins the ISD "development phase", is to develop a sequence of interactive, individualized instruction that is designed to facilitate patients' mastering the previously defined objectives and to evaluate their mastery through the previously developed and calibrated criterion-referenced measures. The instructional sequence should be complete and directed explicitly at the objectives, accurate, brief, highly interactive, and capable of adapting to individual patients' requirements, needs, and interests.

While such a system may seem very simple to develop at first, to institute it can require much preparation. This is no more apparent than in the next step which requires the designing of a system which will interact with the patient in a controllable fashion in an attempt to elicit the aforementioned measurable behaviors from the patient. Merely asking the patient, "Do you understand?" to elicit a "Yes" response is no more effective than the standard informed consent form. Instead, the interaction is designed to force the patient to elicit more affirmative behaviors to prove an understanding of the selected information. It is believed that to do this effectively the training techniques as taught by the incorporated references are desirable. The reasoning for this belief is that while the essential correlation of patient behaviors to legal and medical standards may be readily established, this is not the case for the structuring of queries, questions, or basic stimuli based upon the selected information. The questions must be capable of invoking the desired behavior from the patient. Furthermore, the presentation of the information should be complete, accurate and yet brief so as not to exceed the patient's attention span. Since this is a totally new application for these techniques, these sources are hereby incorporated into the present application by reference.

Once legal and medical standards are estimated, behaviors defined, information selected, and appropriate stimuli developed the system must then be constructed. The preferred embodiment of this invention might make use of various forms of computer-assisted instruction (CAI). This medium provides constant, tireless interaction with the patient, supports a wide variety of visual and auditory displays, is capable of varying the instructional sequence in response to the patient's actions, and faithfully records each of the patient's overt responses. In this case, the system would be designed to use standard computer hardware technology, standard and special purpose computer software, and video disc or digitized audio and/or video, all of which is known and understood by those skilled in training psychology and the computer arts.

The CAI medium may employ text, graphics, still and motion video, and audio in its presentations. The patient may interact with the medium by typing on a standard keyboard, pressing keys on a simplified key pad, touching parts of the visual display (recognized by means of a touch-sensitive screen), indicating parts of the visual display via a mouse, track ball, or light pen, or by answering questions verbally (recognized by voice recognition techniques). The patient may be able to select the language (e.g., English, Spanish) and the vocabulary level used in the presentation.

The CAI instructional sequence may adapt to the patient's requirements in either or both of two ways. First, the CAI instructional sequence will provide frequent opportunities for the patient to respond to content-related questions. These questions may be the criterion-referenced measures described above or they may be lower-level, more specific questions that pertain to components of a single objective. If the patient responds correctly, the program will present new material. If the patient responds incorrectly, the program will review the previously presented material. This review may simply repeat the material or it may present it in a different form. Second, the patient may be asked to indicate how the material is to be presented (e.g., language, vocabulary level, sequence of presentation, depth of presentation, and if and when to return to a previous part of the presentation in order to review it).

The criterion-referenced measures of whether the patient has achieved the objectives may be embedded in the instructional sequence, may follow the presentation of material of each objective, or may be grouped at the end of the instruction. Alternative forms of the measures may also be presented at the beginning of the presentation. In this case, the patient's responses to the pre-instruction measures would be used to determine which parts of the instructional sequence should be presented. This information may be presented to the patient as advice as to which topics to select for instruction or the program may simply route the patient to these topics.

Other learning media may be used of course, such as continuous video or audio tape, records, books, and the like, but they can lack the ability to interact with the patient and to adapt the instructional sequence to the patient's needs. In some instances, however, this could certainly be an acceptable approach for certifying informed consent.

In a fourth ISD phase, the system is implemented in the field (e.g., physicians' offices, clinics, hospitals) and put into use with actual patients. Each patient who interacts with the system receives an instructional sequence tailored to that patient's needs and interests. The anticipated system may be designed to "individualize" the process for each patient. Foreign languages, allegorical presentations, various reading and educational levels, and the like may be programmed into the system in order to allow a range of individuals to be trained by the same system.

During the interaction with each patient, the system will estimate the probability that the patient has mastered each objective. If the estimated probability that the patient has mastered a particular objective does not exceed a predetermined value, the system will present additional instruction pertaining to that objective and repeat the evaluation.

The close-looped training technique may make use of what is known by training psychologists as criterion referenced testing. Through the use criterion referenced testing, acceptable levels of understanding would be established and the patient would be trained to meet or exceed these levels. This training and evaluation process is explained in the paper entitled "An Approach To The Evaluation Of Tailored Testing", presented by Kathleen M. Daubek and Dr. Wilson A. Judd (a co-inventor of the present invention) at the December 1973 annual meeting of the Texas Psychological Association in Dallas, Tex. This paper is hereby incorporated by reference into the present application. In contrast to criterion referenced testing, most education methods utilize a ranking where students are referenced against one another. This is called norm referenced testing. In such a system a score of less than 50% could become an acceptable (passing) level. In the field of informed consent a less than 50% understanding of the risks involved with a certain medical procedure would not be very defensible as having achieved an "informed" state. To accomplish the goal of achieving an informed state, measuring against a predetermined standard—as in criterion referenced testing—is preferred. This allows the standard level to be controlled independent of individual scores. Naturally, the higher the level, the more repeating is likely to be required, but the more defensible the certification of informed consent. This level would be based on the estimated legal and medical standards which apply.

After the selected information is conveyed to the patient and he/she exhibits behaviors appropriate to approximately satisfy the legal and medical requirements for establishing informed consent, the patient is then certified. Certification may take a variety of forms, the most logical perhaps being a printed summary of the selected information, questions, and/or responses, or any part thereof, with standard clauses and a signature line for the patient.

In addition, it is anticipated that the entire interaction between the patient and the system could be captured and stored indefinitely. The value of this aspect would be in later deliberations which may be expedited if substantial proof could be provided as to the patient's understanding of the medical procedure at the time of issuing his/her informed consent. At such a time some form of statistical analysis may be provided as to the probability of the patient's understanding of the various aspects of the medical procedure (ie., prove achievement of objectives).

Figure 3:
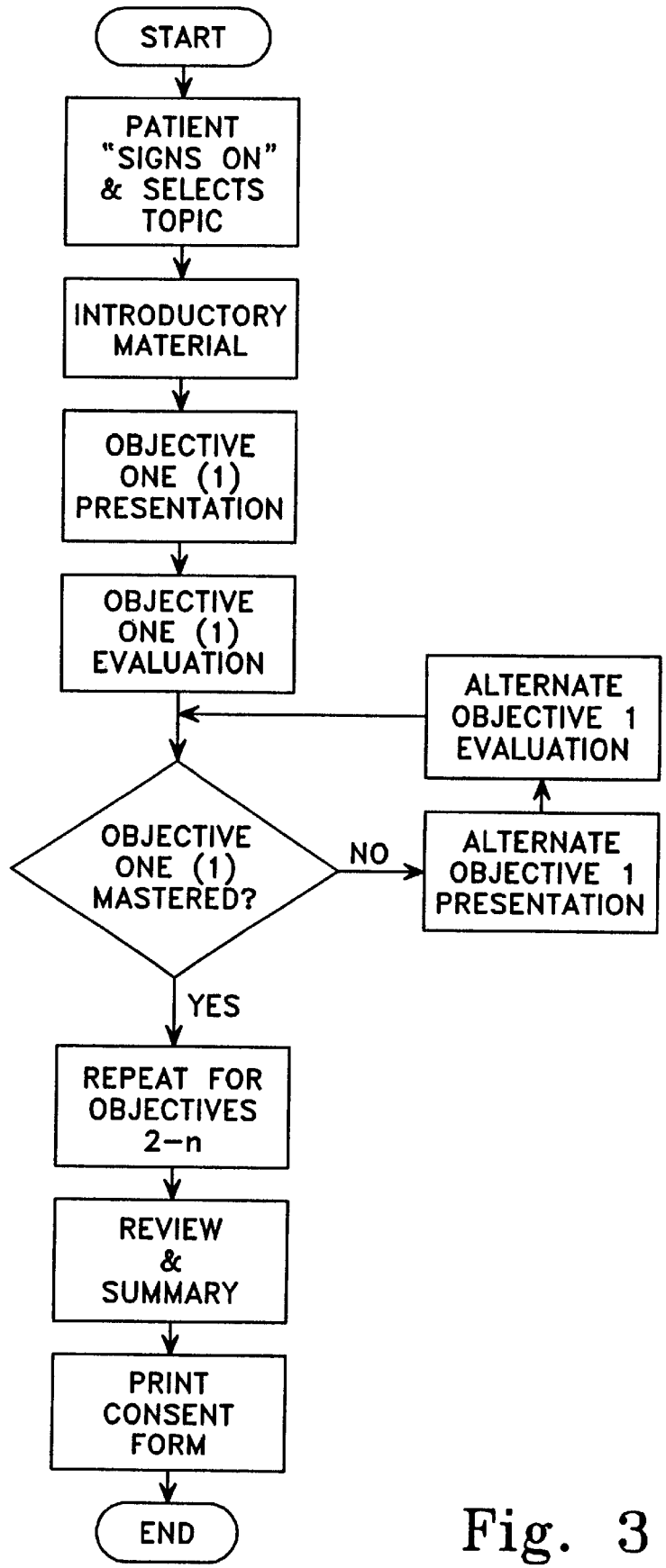
FIG. 3 is a flow chart diagram of one possible simplified interaction process of the present invention.
Figure 4:
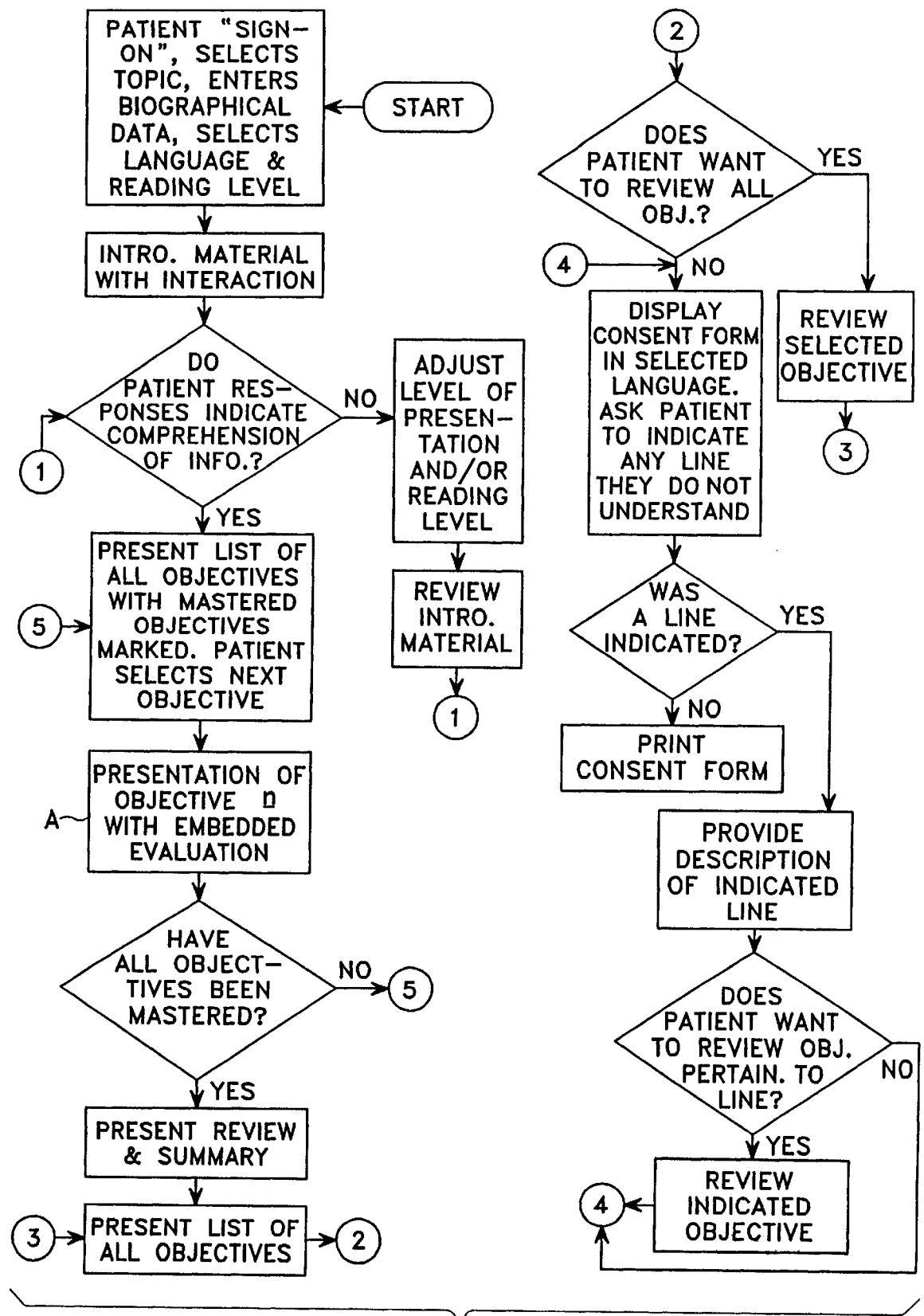
FIG. 4 is a flow chart diagram of one complex interaction process of the present invention.
Figure 5:
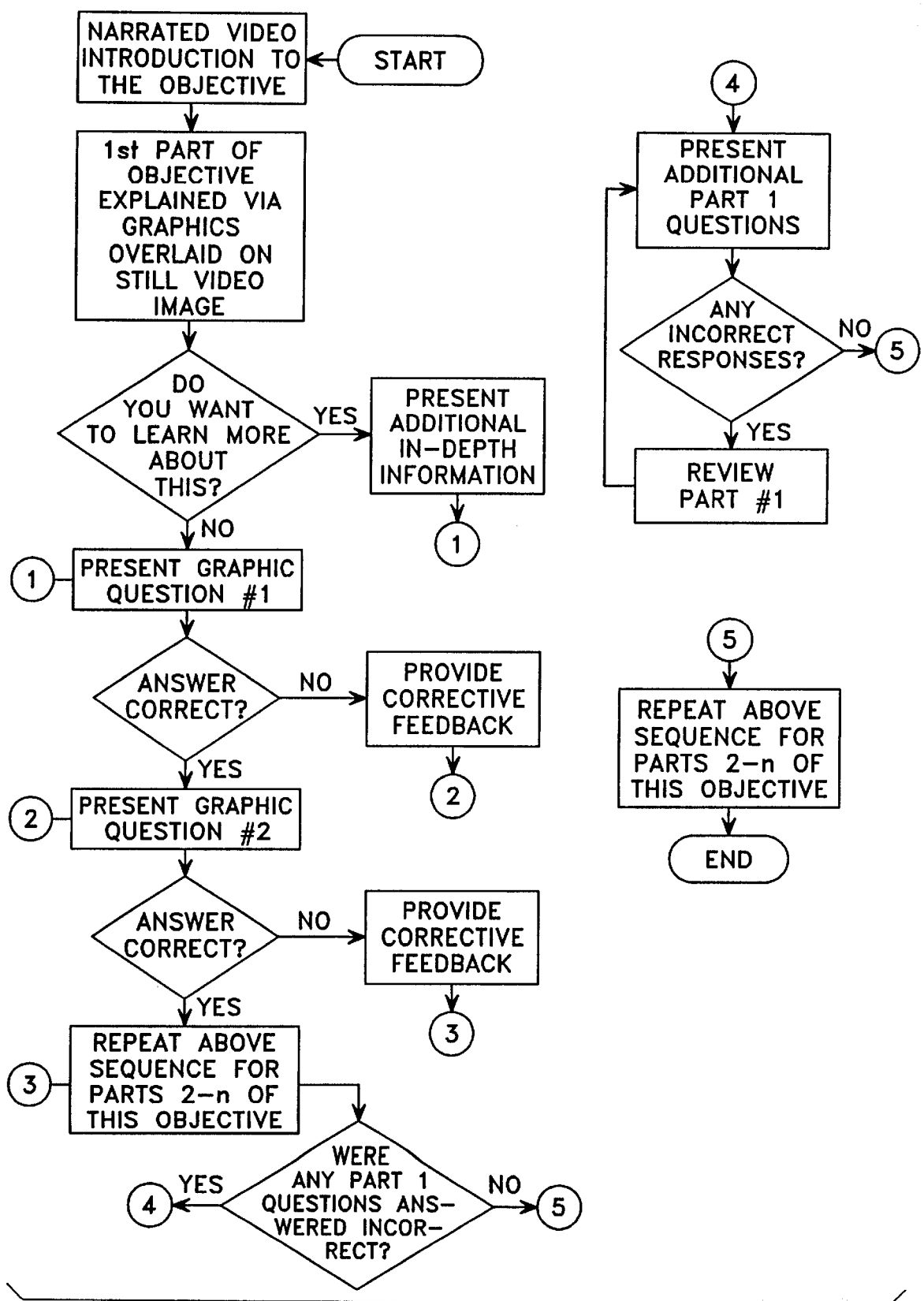
FIG. 5 is a blown-up flow chart diagram of the "presentation of objective n" as shown in box A of FIG. 4.

While development of the system is one aspect of the present invention, its practical application and use is also key for establishing certifiable informed consent. As shown in FIGS. 3, 4 and 5 the preferred embodiments begin with the training of the patient as to the various aspects of the required medical procedure. FIG. 3 illustrates a simple interactive training procedure, while FIG. 4 is illustrative of a more complex embodiment. FIG. 5, a detailed flow chart of box A of FIG. 4, expands on the complex training procedure, and particularly the presentation of each objective. The training technique is broken down into three steps. First, the patient watches and listens to a brief presentation on the medical procedure. The presentation may single out one aspect of the procedure, such as the risks, or it may touch on all the areas of concern. After this brief presentation the patient's comprehension of this information is evaluated in the second step, as discussed earlier. In this step, a set of queries, questions or stimuli may be presented, and time then allowed for the patient to respond. It is anticipated that the queries could be presented as a set of considerations related to the medical procedure, and whereby the patient could then react to the considerations by eliciting a behavioral response—such as touching the video screen, speaking aloud, or the like. The responses, which are measurable behaviors, are measured to approximately coincide with the estimated legal and medical standards to determine the sufficiency of the response. In some cases, responses may be either right or wrong, and in other cases they may be incomplete—that is, for example, if a patient is asked to describe three risks of undergoing the medical procedure as disclosed by the CAI, he/she may only be able to remember two. Wrong and incomplete responses may be adequate to determine an insufficient correlation to the estimated standards. Statistically speaking, as the number of events (patients using the interactive system) increases the measuring of the behaviors may be adjusted to achieve better coincidence between the aspects established through the behavioral responses and those required by legal and medical standards.

The third step involves determining whether the patient's responses sufficiently approximate the legal and medical standards for establishing informed consent—that is, did he/she understand. This may be accomplished, as mentioned previously, by calculating an actual statistical probability that an understanding was achieved by the patient. This probability may then be compared to the predetermined minimum acceptable probability, as explained earlier. If the actual probability is greater than the acceptable this would indicate an acceptable condition, and a second training session may be started. If, however, the actual probability is less than the latter, this might indicate a suboptimal understanding, and require re-training in this objective. Re-training would continue with periodic evaluation until at least the minimum probability of understanding is achieved. This closed-loop training technique will continue until mastery of all aspects presented is achieved by the patient.

The interactive nature of the present invention facilitates learning by the patient, and allows continuous monitoring of patients' levels of knowledge. Furthermore, the dissemination of information through CAI is more conducive to a consistent presentation on a day-to-day, and even patient-to-patient basis. Even though each patient will differ in attitude, intelligence, and other personality traits, the system will adapt its instruction to assure that almost all if not all patients achieve at least the minimum level of knowledge established by the objectives. This relieves the doctor of subjectively trying to determine if a patient truly understands what has been explained. This training approach serves to remove variance from the informed consent procedure due to individual human character. The establishment of the informed consent will be affected by neither a patient's submissive nature, nor a patient's confused state of mind, nor a doctor's busy schedule. Rather, the instructional sequence will present a consistent body of information in a way that accommodates to each patient's needs.

Each of the patient's interactions with the system, each overt response, and the stimulus to which this response was made will be recorded and stored. This data will then be available for two purposes. First, the complete record of an individual patient's interactions, including their final correct responses to the criterion-referenced measures, will be available if a question concerning informed consent should arise at a later date. Second, as part of the fifth or "evaluation phase" of the ISD process, data from multiple patients will be used to analyze and refine and improve both the criterion-referenced measures and the instructional sequences.

To better understand the present invention an example of the process of one embodiment is discussed. Naturally this is a fictitious example, and should not serve to limit the scope of coverage afforded the patent(s) granted on this invention.

EXAMPLE

Scenario: Patient A is about to be admitted to the hospital under the care of Dr. Smith to undergo an abdominal (total) hysterectomy. Before the day of the scheduled surgery Dr. Smith will instruct Patient A to view the disclosure requirements of the procedure on a CAI system (the "invention"). Patient A will agree to view the CAI disclosure.

Procedure: Patient A will be situated, perhaps in a private room or waiting area, to begin review of the CAI. Section I/Part 1: Patient A will be presented background information on abdominal hysterectomies, such as some general information on the medical procedure, and perhaps why it was probably recommended for her condition. At any time during presentation, it may be possible for Patient A to input a command (such as touch the screen, or press a button) to advance to, or return to a specific section/part. Section I/Part 2: Patient A will now be presented with a variety of open-ended questions, such as:

List 2 conditions which may require an abdominal hysterectomy?

What is the average time for an abdominal hysterectomy surgery?

Which of the following types of anesthesia will you require?

Section I/Part 3: Patient A will then be encouraged to respond to each query, and each response evaluated by the system. Patient A answers all three questions correctly. Since no incorrect responses were made, the system estimates that Patient A has mastered this objective and Patient A will then be advanced to the next section.

Section II/Part 1: Patient A will now be presented with the risks inherent to an abdominal hysterectomy, including undergoing a general anesthesia. Patient A decides she is well aware of all the risks and advances the CAI to the next part of the section. Section I/Part 2: Patient A will now be presented with a variety of open-ended questions, such as:

What are the 4 most common complications of an abdominal hysterectomy?

What are 3 critical complications of an abdominal hysterectomy?

Which of the following post-operative discomforts is not typical for an abdominal hysterectomy?

How long is the standard recovery period for an abdominal hysterectomey?

List 3 minor complications which may be experienced after surgery?

Section II/Part 3: Patient A will again be encouraged to respond to each query, and each response evaluated by the system. Of the five questions, Patient A answers four correctly. The question pertaining to common complications was answered incorrectly. Patient A will then automatically be routed to an alternative description of common complications and an alternative form of the question pertaining to common complications will be presented.

This interactive process may continue for sections on the alternative choices to an abdominal hysterectomy, post-operative care, pre-operative preparation, etc. While the patient may be allowed to skip around between sections, certification of informed consent will not be granted until Patient A masters (establishes successful achievement of) each objective. Upon mastery of all objectives, the system will print an informed consent form, listing the key aspects of the interaction, complete with Patient A's name and a signature line, the date and time of consent, and such information. This may be kept for hospital/doctor records, while the complete digital record of the interaction is stored on an internal computer file. Periodically (e.g., monthly) the digital records of all patient interactions will be retrieved from the computer's file and archived for some period. Only after completion of this procedure, in its entirety, including signing of the form, will Patient A be considered to have given her "informed consent" to the abdominal hysterectomy.

The preceding discussion and the claims which follow describe the preferred embodiments of the present invention. Particularly with respect to the claims, it should be understood that changes may be made without departing from its essence. In this regard, it is intended that such changes would still fall within the scope of the present invention. It simply is not practical to describe and claim all possible revisions to the present invention which may be accomplished. To the extent such revisions utilize the essence of the present invention, each would naturally fall within the breadth of protection encompassed by this patent. This is particularly true for the present invention since its basic concepts and understandings are fundamental in nature and can be broadly applied.

We claim:

1. A computer implemented method of establishing certifiable informed consent to an event, said method comprising the steps of:

a. estimating legal standards for establishing informed consent of a participant to said event; then b. defining computer measurable participant behavior which can be approximately coincided with said estimated legal standards; then c. computer training with a first set of instructions said participant on desired aspects of said event through a computer controlled automatic utilization of preprogrammed information stored in a computer; and d. computer interacting with said participant in a standardized fashion through an automatic computer controlled use of preprogrammed information stored in said computer to produce computer measurable participant behavior said computer measurable participant behavior automatically varying said interaction; and e. automatically computer analyzing said participant behavior; then f. determining whether said training should be adjusted depending on said analyzing said participant behavior;

g. identifying which portions of said training should be adjusted;

h. modifying to create at least one modified portion of said training to a different set of instructions than said first set of instructions based on said step of determining whether said training should be adjusted;

i. additionally computer interacting with said participant in a standardized fashion through an automatic computer controlled use of preprogrammed information stored in said computer to produce computer measurable participant behavior; and j. additionally computer analyzing said participant behavior; then k. additionally determining whether said training should be adjusted depending on said analyzing said participant behavior; and l. computer providing an automatic indication of centifiability that said participant likely meets said legal standards for establishing informed consent to said event.

2. A computer implemented method of establishing certifiable informed consent as described in claim 1 wherein said step of defining comprises the steps of:

a. translating said legal standards to computer measurable behavior; then b. evaluating the validity of the correlation between said standards and said behavior.

3. A computer implemented method of establishing certifiable informed consent as described in claim 2 wherein said step of defining further comprises the step of continuously refining said step of measuring to achieve better approximation between said standards and said computer measurable behavior.

4. A computer implemented method of establishing certifiable informed consent as described in claim 1 wherein said step of computer providing an automatic indication of computer certification comprises the step of achieving defined computer measurable participant behavior which approximately coincide with said legal standards.

5. A computer implemented method of establishing certifiable informed consent as described in claim 4 wherein said step of computer providing an automatic indication of computer certification further comprises the step of statistically establishing a probability of satisfaction.

6. A computer implemented method of establishing certifiable informed consent as described in claim 5 wherein said step of statistically establishing comprises the steps of:

a. repetitively testing said participant through use of said computer to elicit responses; then b. evaluating said responses through use of said computer.

7. A computer implemented method of establishing certifiable informed consent as described in claim 1 wherein said step of computer providing an automatic indication of computer certification comprises proving mastery of aspects of said event by communicating with said computer.

8. A computer implemented method of establishing certifiable informed consent as described in claim 7 wherein said step of proving further comprises the step of storing said computer measurable participant behavior.

9. A computer implemented method of establishing certifiable informed consent as described in claim 1 further comprising the steps of:

a. analyzing said event procedure comprising the steps of:
      (1) compiling fundamental information on said event; then
      (2) selecting information which may be stored within a computer and which is legally likely to be necessary for informed consent; then b. designing a computer stored system utilizing an instructional system development model for computer training said participant on said selected information.

10. A computer implemented method of establishing certifiable informed consent as described in claim 9 further comprising automatically periodically performing computer controlled criterion referenced testing on said participant wherein said testing automatically varies said computer controlled presentation.

11. A computer implemented method of establishing certifiable informed consent as described in claim 10 wherein said step of automatically performing periodic, computer controlled criterion referenced testing comprises the steps of:

a. posing a set of applicable considerations to said participant through use of said computer, wherein said considerations relate to said selected information; then b. requiring said participant to respond to said considerations by communicating with said computer.

12. A computer implemented method of establishing certifiable informed consent as described in claim 1 wherein said step of determining whether said training should be adjusted comprises the steps of:

a. predetermining an acceptable statistical probability for indicating a correlation between said participant response and said legal standards; then b. periodically computing an actual statistical probability of said correlation through use of said computer; then c. comparing said actual probability to said acceptable probability through use of said computer; then d. adjusting said training until said actual probability is at least equal to said acceptable probability.

13. A computer implemented method of establishing certifiable informed consent for a medical procedure, said method comprising the steps of:

a. estimating legal and medical standards for establishing informed consent to said procedure; then b. defining computer measurable patient behavior which can be approximately coincided with said estimated legal and medical standards; then c. computer training with a first set of instructions said patient on desired aspects of said medical procedure through a computer controlled automatic utilization of preprogrammed information stored in a computer; and d. computer interacting with said patient in a standardized fashion through an automatic computer controlled use of preprogrammed information stored in said computer to produce computer measurable patient behavior said computer measurable patient behavior automatically varying said interaction; and e. automatically computer analyzing said patient behavior; then f. determining whether said training should be adjusted depending on said analyzing said patient behavior;

g. identifying which portions of said training should be adjusted;

h. modifying to create at least one modified portion of said training to a different set of instructions than said first set of instructions based on said step of determining whether said training should be adjusted;

i. additionally computer interacting with said patient in a standardized fashion through an automatic computer controlled use of preprogrammed information stored in said computer to produce computer measurable patient behavior said computer measurable patient behavior automatically varying said interaction; and j. additionally computer analyzing said patient behavior; then k. additionally determining whether said training should be adjusted depending on said analyzing said patient behavior; and l. computer providing an automatic indication of certifiability that said patient likely meets said legal and medical standards for establishing informed consent to said procedure.

14. A computer implemented method of establishing certifiable informed consent as described in claim 13 wherein said step of defining comprises the steps of:
  a. translating said legal and medical standards to computer measurable behavior; then
  b. evaluating the validity of the correlation between said standards and said behavior.

15. A computer implemented method of establishing certifiable informed consent as described in claim 13 wherein said step of computer providing an automatic indication of computer certification comprises the step of achieving defined computer measurable patient behavior which approximately coincide with said legal and medical standards.

16. A computer implemented method of establishing certifiable informed consent as described in claim 15 wherein said step of computer providing an automatic indication of computer certification further comprises the step of statistically establishing a probability of satisfaction.

17. A computer implemented method of establishing certifiable informed consent as described in claim 13 further comprising the steps of:
  a. analyzing said medical procedure comprising the steps of:
    (1) compiling fundamental information on said medical procedure; then
    (2) selecting information which may be stored within a computer and which is legally likely to be necessary for informed consent; then
  b. designing a computer stored system utilizing an instructional system development model for computer training said patient on said selected information.

18. A computer implemented method of establishing certifiable informed consent as described in claim 17 further comprising automatically periodically performing computer controlled criterion referenced testing on said patient wherein said testing automatically varies said computer controlled presentation.

19. A computer implemented method of establishing certifiable informed consent as described in claim 18 wherein said step of automatically performing periodic, computer controlled criterion referenced testing comprises the steps of:
  a. posing a set of applicable considerations to said patient through use of said computer, wherein said considerations relate to said selected information; then
  b. requiring said patient to respond to said considerations by communicating with said computer.

20. A computer implemented method of establishing certifiable informed consent as described in claim 13 wherein said step of determining whether said training should be adjusted comprises the steps of:
  a. predetermining an acceptable statistical probability for indicating a correlation between said patient response and said legal and medical standards; then
  b. periodically computing an actual statistical probability of said correlation through use of said computer; then
  c. comparing said actual probability to said acceptable probability through use of said computer; then
  d. adjusting said training until said actual probability is at least equal to said acceptable probability.

* * * * *